United States Patent [19]

Ashby

[11] 4,390,660
[45] Jun. 28, 1983

[54] ULTRAVIOLET LIGHT ABSORBING COMPOSITIONS

[75] Inventor: Bruce A. Ashby, Schenectady, N.Y.

[73] Assignee: General Electric Company, Waterford, N.Y.

[21] Appl. No.: 328,922

[22] Filed: Dec. 9, 1981

Related U.S. Application Data

[62] Division of Ser. No. 154,621, May 30, 1981, Pat. No. 4,321,400.

[51] Int. Cl.³ .......................... C08K 5/13; C08K 5/16
[52] U.S. Cl. .................................. 524/721; 524/188; 524/588; 524/385; 428/412; 556/436
[58] Field of Search .................. 524/588, 721, 385

[56] References Cited

U.S. PATENT DOCUMENTS

| | | | |
|---|---|---|---|
| 3,708,225 | 1/1973 | Misch et al. | 351/160 |
| 3,976,497 | 8/1976 | Clark | 106/287 SE |
| 3,986,997 | 10/1976 | Clark | 260/29.2 M |
| 4,051,161 | 9/1977 | Proskow | 260/448.8 R |
| 4,177,315 | 12/1979 | Ubersax | 428/336 |
| 4,188,451 | 2/1980 | Humphrey, Jr. | 428/331 |
| 4,278,804 | 7/1981 | Ashby et al. | 556/436 |

Primary Examiner—Joseph L. Schofer
Assistant Examiner—J. M. Reddick
Attorney, Agent, or Firm—Hedman, Casella, Gibson, Costigan & Hoare

[57] ABSTRACT

There are provided ultraviolet light absorbing agents of the formula

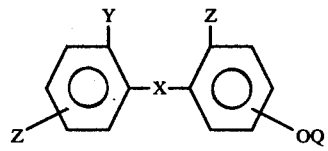

wherein:
X is $>C=O$, or

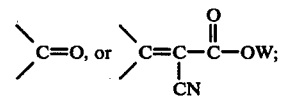

Y is H or OH;
Z is H, OH, OQ or OW, where at least one Z is OH if Y is H;
Q is $-CONH(CH_2)_3Si(R_2)_x(OR_1)_y$ or $-CONH(CH_2)_3Si(R_2)_x(OCOR_1)_y$; and
W is $-C_mH_{2m+1}$;

where $x=0$, 1 or 2, $y=1$, 2 or 3, $x+y=3$, $R_1$ and $R_2$, independently are each alkyl having 1 to 6 carbon atoms and $m=1$ to 18. Also provided are organopolysiloxane protective coating compositions containing said ultraviolet light absorbing agents having unique utility for protecting transparent plastic articles.

8 Claims, No Drawings

ULTRAVIOLET LIGHT ABSORBING COMPOSITIONS

This is a division of application Ser. No. 154,621 filed May 30, 1981 U.S. Pat. No. 4,321,400.

This invention relates to new, improved ultraviolet light absorbing agents, as well as to compositions containing such agents and to articles coated with such compositions. The novel compounds of this invention are silanol-reactive alkoxysilyl- or alkanoyloxysilyl alkyl carbamyl adducts of aromatic ultraviolet absorbing agents.

BACKGROUND OF THE INVENTION

The use of transparent plastic materials in place of glass panels is becoming more widespread. For instance, transparent glazing made of synthetic organic polymers is now employed more frequently in transportation, such as trains, buses and the like, in optical equipment, and in construction materials. In comparison with glass, transparent plastics are shatter-resistant and lighter in weight.

While enjoying the foregoing advantages, transparent plastics are nevertheless susceptible to scratching and marring on the surface, which impairs visbility and detracts from the physical appearance. Moreover, transparent plastics tend to undergo discoloration upon prolonged exposure to ultraviolet light, e.g., sunlight.

Attempts have been made to improve the abrasion resistance of transparent plastics. It has been proposed, for instance, that mar- or scratch-resistant coatings for such plastics can be prepared from mixtures comprising silica and hydrolyzable silanes in a suitable medium such as alcohol and water. Such protective coatings are described in Misch et al., U.S. Pat. No. 3,708,225, Clark, U.S. Pat. No. 3,986,997 and U.S. Pat. No. 3,976,497, and Ubersax, U.S. Pat. No. 4,177,315. Other scratch-resistant protective coatings are described in copending commonly assigned application Ser. No. 964,910, filed Nov. 30, 1978 and Frye, U.S. Pat. No. 4,277,287. Typically, these are applied to the surface of the transparent plastic and heat cured in situ.

Attempts have also been made to reduce the tendency of the coatings on transparent plastics toward deterioration on exposure to sunlight and the like by incorporating in the coating compositions materials which absorb ultraviolet light rays. A disadvantage of many such ultraviolet light absorbing materials is that they often escape from the compositions, e.g., by volatilization, usually during the heat curing cycle. Efforts to overcome this defect by using ultraviolet light absorbing materials having higher molecular weights, e.g., American Cyanamid's Cyasorb UV-531, have not been entirely successful.

Proskow, U.S. Pat. No. 4,051,161, discloses an alternative approach and this is to use a silane-fluorohydroxy copolymer coating with a silanol-reactive functional derivative of an aromatic ultraviolet light-absorbing compound. As the agent to contribute the silanol-reactive functional group it is proposed to use a complex epoxy-silane compound. The Proskow coating is not the preferred, less complex silica-hydrolyzable silane coating of the earlier mentioned citations. Other commonly assigned, concurrently filed applications also deal with functionalized uv screens. See Ashby et al., U.S. Pat. No. 4,278,804; copending U.S. application Ser. No. 154,623 (Ching), filed May 30, 1980; copending U.S. application Ser. No. 154,625 (Ching), filed May 30, 1980; and U.S. application Ser. No. 154,626 (Ching), now allowed, filed May 30, 1980. The disclosures of the foregoing patents and applications are incorporated herein by reference.

It has now been discovered that reactive functional derivatives of aromatic ultraviolet light-absorbing agents with superior properties in all important respects can be obtained by using alkoxysilylalkyl- or alkanoyloxysilylalkylcarbamyl functional groups, and that these are useful in the less complex systems, i.e., not the copolymer coating systems called for in U.S. Pat. No. 4,051,161.

With the new compounds of this invention scratch-resistant coatings for transparent plastics can be made more resistant to discoloration upon exposure to ultraviolet light. Because such modified ultraviolet light absorbers are adapted to coreact with the polysiloxane of the scratch-resistant coating composition, there is a much reduced tendency of such materials to escape or oxidize during thermal processing. This provides substantial economy of use in comparison with the prior art.

DESCRIPTION OF THE INVENTION

According to this invention, there are provided new ultraviolet light absorbing agents having the following formula:

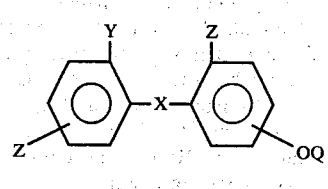

wherein:
X is $>C=O$, or

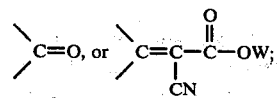

Y is H or OH;
Z is H, OH, OQ or OW, where at least one Z is OH if Y is H;
Q is $-CONH(CH_2)_3Si(R_2)_x(OR_1)_y$ or $-CONH(CH_2)_3Si(R_2)_x(OCOR_1)_y$; and
W is $-C_mH_{2m+1}$;
where $x=0$, 1 or 2, $y=1$, 2 or 3, $x+y=3$, $R_1$ and $R_2$, independently, are each alkyl having 1 to 6 carbon atoms, and preferably methyl and $m=1$ to 18.

Within the foregoing class, the following compounds are preferred:

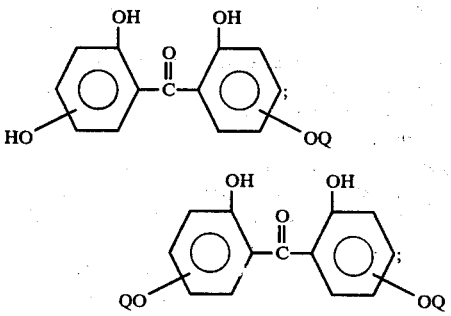

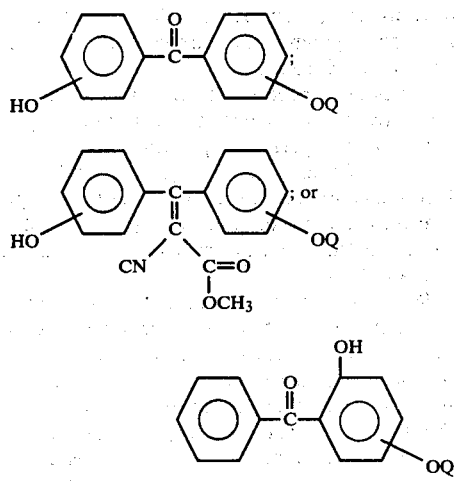

where Q is —CONH(CH$_2$)$_3$Si(OCH$_3$)$_3$, —CONH(CH$_2$)$_3$SiCH$_3$(OCH$_3$)$_2$ or —CONH(CH$_2$)$_3$Si(CH$_3$)$_2$(OCH$_3$). Special mention is made of the compound 4-[γ-(trimethoxysilyl)propylcarbamoyloxy]2,2',4'-trihydroxybenzophenone.

This invention also includes coating compositions comprising an effective amount of the described ultraviolet light absorbing agents and a dispersion of colloidal silica in an aliphatic alcohol-water solution of the partial condensate of a silanol having the formula RSi(OH)$_3$, where R is selected from the group consisting of alkyl having from 1 to 3 carbon atoms and aryl, at least 70 percent by weight of the silanol being CH$_3$Si(OH)$_3$. The dispersion contains from 10 to 50 percent by weight of solids, said solids consisting essentially of 10 to 70 percent by weight of colloidal silica and from 30 to 90 percent by weight of the partial condensate. In most preferred embodiments, the dispersion has a pH of from 7.1 to about 7.8.

The ultraviolet light absorbing agents of this invention can be prepared, for example, by a convenient method starting with a compound having the formula

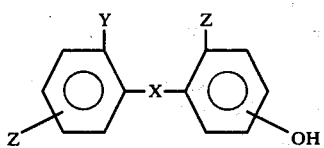

in which X, Y and Z are as defined above. In this method the above compound is reacted in a solvent with an isocyanatopropylsilane having the formula OCN(CH$_2$)$_3$Si(R$_2$)$_x$(OR$_1$)$_y$ or OCN(CH$_2$)$_3$—Si(R$_2$)$_x$-(OCOR$_1$)$_y$. R$_1$, R$_2$, X, and Y are defined above. Of course, other methods will be obvious to those skilled in this art.

The reaction of the isocyanatopropylsilanes and the phenolic compound can be run, generally, in the range of 50° to 150° C. for a period of 1 to 6 hours. Yields of 85–98% are typical.

The isocyanatopropylsilanes for use in the above reaction are prepared, in good yield, by the platinum catalyzed reaction of an alkenyl isocyanate with the corresponding alkoxysilyl hydride or acyloxysilyl hydride. Alternatively, these are prepared by reacting alkenylisocyanate with the corresponding chlorosilane followed by alkoxylation. Procedures for preparation of the foregoing are described in the literature, e.g., by B. A. Ashby, in the Journal of Chemical and Engineering Data, 18, No. 2, page 238 (1973), which is incorporated herein by reference.

The coating compositions of this invention are prepared by hydrolyzing an alkyltrialkoxysilane or aryltrialkoxysilane having the formula RSi(OR)$_3$, where R is alkyl having 1 to 3 carbon atoms, or aryl, preferably phenyl, in an aqueous dispersion of colloidal silica to obtain a reaction product, and adding the described ultraviolet light absorbers to the resulting reaction product.

In general, the aqueous dispersion of colloidal silica is characterized by a particle size of from 5 to 150 millimicrons, and preferably from 10 to 30 millimicrons average diameter. Such dispersion are known in the art. Commercially available materials include Ludox (DuPont) and Nalcoag (NALCO Chemical Co.). These are available in the form of acidic or basic hydrosols. With regard to this invention, if the pH of the coating composition is basic, then usually a basic colloidal silica sol is preferred for use in the composition. On the other hand, colloidal silicas which are initially acidic but which have been adjusted to be basic can also be used. It has been found that colloidal silica having a low alkali content, e.g., less than 0.35% by weight as Na$_2$O, provides a more stable coating composition, and these are preferred.

In preparing the compositions, the aqueous dispersion of colloidal silica is added to a solution of a small amount, e.g., from 0.07 to 0.10 percent by weight, of an alkyltriacetoxysilane in alkyltrialkoxysilane or aryltrialkoxysilane. The temperature of the reaction mixture is kept in the range between 20° to 40° C., preferably below 25° C. A reaction time of about six to eight hours is usually sufficient to react enough of the trialkoxysilane such that the initial two-phase liquid mixture has been converted to a single liquid phase in which the silica is dispersed. Hydrolysis is permitted to continue for a period of 24 to 48 hours, depending on the desired final viscosity. As a rule, the longer the time permitted for hydrolysis, the higher the final viscosity.

During the preparation of the coating compositions, the alkyl triacetoxysilane is employed to buffer the viscosity of the initial two-phase liquid reaction mixture, and also to regulate the hydrolysis rate. Preferred are those alkyltriacetoxysilanes in which the alkyl group contains from 1 to 6 carbon atoms, and especially 1 to 3 carbon atoms. Methyltriacetoxysilane is the most preferred. Although alkyltriacetoxysilanes are preferred for use, it is to be understood that glacial acetic acid or other acids may be used instead. Such other acids include organic acids, such as propionic, butyric, citric, benzoic, formic, oxalic, and the like.

After hydrolysis has been completed, the solids content of the coating composition is adjusted by adding alcohol to the reaction mixture. Suitable alcohols include lower aliphatics, e.g., having 1 to 6 carbon atoms, such as methanol, ethanol, propanol, isopropanol, n-butyl alcohol, t-butyl alcohol, and the like, or mixtures thereof. Isobutanol is preferred. The solvent system, i.e., mixture of water and alcohol, should contain from about 20 to 75 percent by weight of the alcohol to ensure that the partial siloxanol condensate is soluble.

Optionally, additional water-miscible polar solvents, e.g., acetone, butyl cellosolve, or the like, can be included in minor amounts, usually no more than 20 percent by weight of the solvent system.

After adjustment with solvent, the coating composition preferably has a solids content of from about 18 to about 25 percent by weight, especially preferably about 20 percent by weight of the total composition.

The coating composition has a pH of from about 3.5 to about 8, preferably from about 7.1 to about 7.8, and especially preferably from about 7.2 to about 7.8. If necessary, a base, such as dilute ammonium hydroxide, or weak acid, such as acetic acid, is added to adjust the pH within this range.

The silanetriols, RSi(OH)$_3$, are formed in situ as a result of admixing the corresponding trialkoxysilanes with the aqueous medium, i.e., the aqueous dispersion of colloidal silica. Examples of the trialkoxysilanes are those containing methoxy, ethoxy, isopropoxy and n-butoxy substituents which, upon hydrolysis, generate the silanetriols and further liberate the corresponding alcohol, e.g., methanol, ethanol, isopropanol, n-butanol, and the like. In this way, at least a portion of the alcohol content present in the final coating composition is provided. Upon generation of the hydroxyl substituents to form

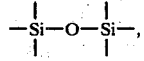

bonding occurs. This condensation, which takes place over a period of time, is not exhaustive but rather the siloxane retains a quantity of silicon-bonded hydroxyl groups which render the polymer soluble in the alcohol-water solvent mixture. This soluble partial condensate can be characterized as a siloxanol polymer having at least one silicon-bonded hydroxyl group for every three

units.

The portion of the coating composition which consists of non-volatile solids is a mixture of colloidal silica and the partial condensate (or siloxanol) of a silanol. The major portion or all of the partial condensate or siloxanol is obtained from the condensation of CH$_3$Si(OH)$_3$. Depending on the input of ingredients to the hydrolysis reaction, minor amounts of partial condensate can be obtained, e.g., such as from the condensation of CH$_3$Si(OH)$_3$ with C$_2$H$_5$Si(OH)$_3$ or C$_3$H$_7$Si(OH)$_3$, of CH$_3$Si(OH)$_3$ with C$_6$H$_5$Si(OH)$_3$, or mixtures of the foregoing. For best results, it is preferred to use only methyltrimethoxysilane (thus generating all mono-methylsilanetriol) in preparing the coating compositions. In the preferred embodiments, the partial condensate is present in an amount of from about 55 to 75 percent by weight, (the colloidal silica being present in an amount of from total weight of solids in the solvent comprising a mixture of alcohol and water. The alcohol comprises from about 50% to 95% by weight of the solvent mixture.

The coating compositions completely cure to hard coatings at a temperature of about 120° C., without the necessity of a curing catalyst. If milder curing conditions are desired, it is preferred to include a buffered latent condensation catalyst. Such catalysts are known to those skilled in the art. Examples include alkali metal salts of carboxylic acids, such as sodium acetate, potassium formate, and the like, amine carboxylates, such as dimethylamine acetate, ethanolamine acetate, dimethylaniline formate, and the like; quaternary ammonium carboxylates, such as tetramethylammonium acetate, benzyltrimethylammonium acetate, and the like; metal carboxylates, such as tin octoate; amines, such as triethylamine, triethanolamine, pyridine, and the like; and alkali hydroxides, such as sodium hydroxide, ammonium hydroxide, and the like. It should be noted that commercially available colloidal silicas, particularly those having a basic pH, i.e., above 7, contain free alkali metal base, and alkali metal carboxylate catalysts are generated in situ during hydrolysis.

The amount of the curing catalyst can vary widely, depending upon particular requirements. In general, the catalyst is present in an amount of from about 0.05 to about 0.5 and preferably about 0.1 percent by weight of the total coating composition. Such compositions are curable on the substrate within a brief period of time, e.g., from 30 to 60 minutes, using temperatures in the range from about 85° to about 120° C. A transparent, abrasion-resistant coating results.

The ultraviolet light-absorbing reaction products of this invention are added to the described coating composition before, during or after hydrolysis, and also before or after addition of solvent to adjust the solids. In preferred compositions, the ultraviolet light absorbing agents of this invention are used in amounts from about 1.0 to about 25.0, preferably from 5.0 to 10.0 parts by weight per 100 parts by weight of said composition on a solids basis.

Other ingredients may also be added. Special mention is made of polysiloxane-polyether copolymers, which control flow and prevent flow marks, dirt marks, and the like, on the coating surface. Such materials also increase the stress cracking resistance of the coating.

Preferred for use in this invention are liquid polysiloxane-polyether copolymers having the following formula:

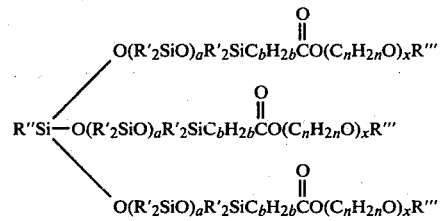

wherein R' and R'' are monovalent hydrocarbons, R''' is lower alkyl, preferably alkyl having 1 to 7 carbon atoms, a is at least 2, preferably 2 to about 40, b is from 2 to 3, n is from 2 to 4, and x is at least 5, preferably 5 to 100.

By way of illustration, R' and R'', independently, are alkyl, such as methyl, ethyl, propyl, butyl, octyl, and the like; cycloalkyl, such as cyclohexyl, cycloheptyl, and the like; aralkyl, such as benzyl, phenylethyl, and the like; alkenyl or cycloalkenyl, such as vinyl, allyl, cyclohexenyl, and the like; and halogenated derivatives of any of the foregoing, such as chloromethyl, chorophenyl, dibromophenyl, and the like. Illustratively, R''' is methyl, ethyl, propyl, butyl, isobutyl, amyl, and the like.

The preparation of the above polysiloxane-polyether copolymer is described in U.S. Pat. No. 3,629,165, incorporated herein by reference. Suitable commercially available materials are SF-1066 and SF-1141, from General Electric Company, Mallinckrodt's BYK-300, Union Carbide's L-540 and Dow-Corning's DC-190.

Other ingredients, such as thickening agents, pigments, dyes, and the like, can also be included for their conventionally employed purposes. These are added to the compositions after hydrolysis has been completed.

The coating compositions can be applied to the primed surface of an article using conventional methods, e.g., as by flow coating, spraying or dip coating, to form a continuous film or layer thereon. The cured compositions are useful as protective coatings on a wide variety of surfaces, either transparent or opaque, including plastic surfaces and metal surfaces. Examples of such plastics include synthetic organic polymeric substrates, such as acrylic polymers, e.g., poly(methylmethacrylate), and the like; polyesters, e.g., poly(ethylene terephthalate), poly(butylene terephthalate), and the like; polyamides, polyimides, acrylonitrile-styrene copolymers; styrene-acrylonitrile-butadiene terpolymers; polyvinyl chloride; butyrates, polyethylene, and the like.

Special mention is made of the polycarbonates, such as those polycarbonates known as LEXAN®, available from General Electric Company, including transparent panels made of such materials. The compositions of this invention are especially useful as protective coatings on the primed surfaces of such articles.

Suitable substrates also include both bright and dull metal surfaces, such as aluminum or sputtered chromium alloys. In addition, the coating compositions of this invention can be applied on other types of surfaces such as wood, leather, glass, ceramics, textiles, and the like.

A hard coating is obtained by removing the solvent and other volatile materials from the composition. The coating air-dries to a substantially tack-free condition, but heating in the range of 75° C. to 200° C. is necessary to obtain condensation of residual silanols in the partial condensate. Final cure results in the formation of silsesquioxane(RSiO$_{3/2}$). In the cured coating, the ratio of RSiO$_{3/2}$ units to SiO$_2$ ranges from about 0.43 to about 9.0, and more usually from 1 to 3. A cured coating having a ratio of RSiO$_{3/2}$ to SiO$_2$, where R is methyl, equal to 2, is most preferred. The coating thickness can be varied, but, in general, the coating will have a thickness in the range between 0.5 and 20 microns, more usually from 2 to 10 microns.

The coating compositions described herein can be applied with good adhesion to virtually any surface to provide protectively coated articles in accordance with this invention.

DESCRIPTION OF THE SPECIFIC EMBODIMENTS

The compounds, compositions and articles of this invention are illustrated in the following examples. All parts are by weight.

EXAMPLE 1

A solution of 24.6 parts of 2,2',4,4'-tetrahydroxybenzophenone in 95 parts of N,N-dimethylformamide is prepared. To this solution is added 20.5 parts of γ-isocyanotopropyltrimethoxysilane and a trace of stannous octoate. The mixture is heated for one hour at 150° C. after which time infrared analysis records the absence of NCO absorption at 2280 cm$^{-1}$ and completion of the reaction. The solvent is removed by vacuum distillation at 29 mm to a pot temperature of 99° C. There is obtained 44.3 parts of a crystalline residue corresponding to 98% yield of

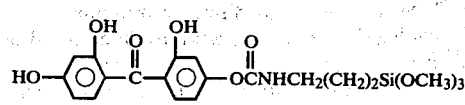

Twenty-two and one-tenths parts by weight of Ludox LS silica sol (DuPont, an aqueous dispersion of colloidal silica having an average particle size of 12 millimicrons and a pH of 8.4), is added to a solution of 0.1 part by weight of methyltriacetoxysilane in 26.8 parts by weight of methyltrimethoxysilane. The temperature of the reaction mixture is kept at 20° to 25° C. The hydrolysis is allowed to continue for 24 hours. The resulting reaction mixture has a solids content of 40.5 percent. Isobutanol is added to bring the solids content to 20 percent. The pH of the product is about 7.2.

The above compound and coating composition are mixed to form a single composition which is flow-coated onto a transparent LEXAN® poly(bisphenol-A carbonate) panel which has been primed with a thermosetting acrylic emulsion. The panel is air dried for 30 minutes, and then cured at 120° C. for one hour. After 500 Taber Abraser cycles (500 g. load, CS-10F wheels), according to ANSI-Z26.1—1977 section 5.17, the change in percent haze (Δ% H) is found to be 1.8. The sample passes the cross-hatched adhesion test (DIN-53-151) after 7 days immersion in water at 65° C. The sample also passes the cross-hatched adhesion test after 1000 hours under R-S Lamp exposure on a rotating platform (3 revolutions per minute), spaced 10 inches from the faces of an array of 6 lamps arranged at 120° from one another.

In addition to the foregoing abrasion test results, it is observed that the coated panel does not discolor upon exposure to ultraviolet light for a period of 600 hours when tested by ASTM D 1925 on a Hunter Tristimulus colorimeter.

EXAMPLE 2

The procedure of Example 1 is repeated, except that 5 parts by weight of SF-1066, General Electric Company, a polysiloxane-polyether copolymer, is included in the composition before coating. Substantially the same abrasion resistance and ultraviolet absorbing properties in the cured coating are obtained. In addition, the hard coating is smooth and clear and shows no signs of flow marks or stress cracking.

Other modifications and variations of the invention are possible in view of the above disclosure. It is to be understood, therefore, that changes may be made in the particular embodiments described without departing from the principles of the invention, and without sacrifice to the chief benefits.

I claim:
1. An aqueous coating composition, which comprises:
   (a) a dispersion of a colloidal silica in a solution of the partial condensate of a silanol having the formula RSi(OH)$_3$, where R is selected from the group consisting of alkyl having 1 to 3 carbon atoms and aryl, at least 70 weight percent of which is CH$_3$Si(OH)$_3$, in a mixture of an aliphatic alcohol and water, said dispersion containing from 10 to 50 percent by weight of solids, said solids consisting essentially of 10 to 70 percent by weight of the colloidal silica and 30 to 90 percent by weight of the partial condensate, and (b) an effective amount of an ultraviolet light absorbing agent consisting of a compound having the formula

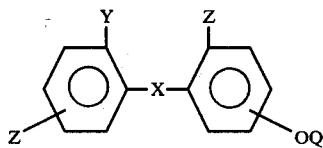

wherein:

X is >C=O, or

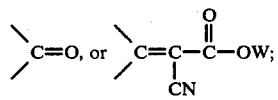

Y is H or OH;

Z is H, OH, OQ or OW, where at least one Z is OH if Y is H;

Q is —CONH(CH$_2$)$_3$Si(R$_2$)$_x$(OR$_1$)$_y$ or —CONH(CH$_2$)$_3$Si(R$_2$)$_x$(OCOR$_1$)$_y$; and W is C$_m$H$_{2m+1}$ where x=0, 1 or 2, y=1, 2 or 3, x+y=3, and R$_1$ and R$_2$, independently, are alkyl having 1 to 6 carbon atoms and m=1 to 18.

2. A composition as defined in claim 1, which contains from about 5.0 to about 10.0 parts by weight of the ultraviolet light absorbing agent per 100 parts by weight of said composition, on a solids basis.

3. A composition as defined in claim 1, in which the ultraviolet light absorbing agent is selected from

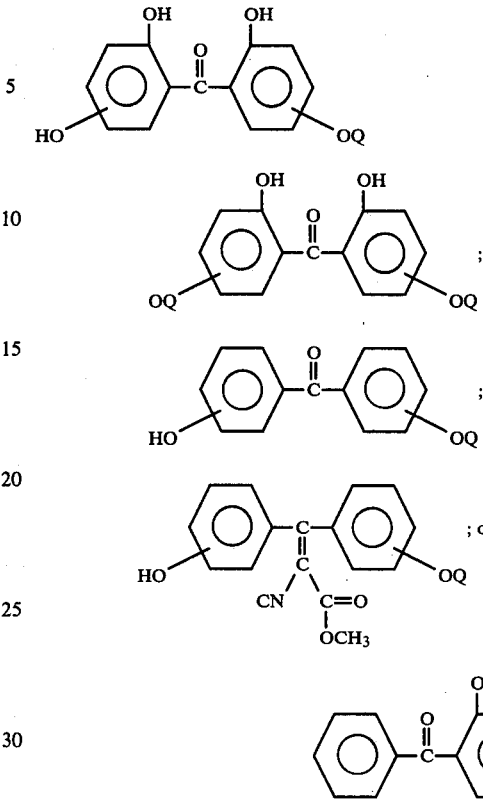

where Q is —CONH(CH$_2$)$_3$Si(OCH$_3$)$_3$, —CONH(CH$_2$)$_3$SiCH$_3$(OCH$_3$)$_2$ or —CONH(CH$_2$)$_3$Si(CH$_3$)$_2$(OCH$_3$).

4. A composition as defined in claim 3 wherein said ultraviolet light absorbing agent is 4-[γ-(trimethoxysilyl)propylcarbamyloxy]-2,2′,4′-trihydroxybenzophenone.

5. A composition as defined in claim 1, in which the aliphatic alcohol comprises a mixture of methyl alcohol and isobutyl alcohol.

6. A composition as defined in claim 1, in which the silanol is CH$_3$Si(OH)$_3$.

7. A composition as defined in claim 1, which also includes a polysiloxane-polyether copolymer.

8. A composition as defined in claim 1, in which the colloidal dispersion contains from about 18 to about 25% by weight of solids consisting essentially of from about 25 to about 45% by weight of the colloidal silica and from about 55 to about 75% by weight of the partial condensate.

* * * * *